United States Patent [19]

Rollick et al.

[11] Patent Number: 4,737,155
[45] Date of Patent: Apr. 12, 1988

[54] STABILIZERS FOR IMPROVING THE OZONE FASTNESS OF DYES WITH OXADIAZINE-4-THIONE OR TRIAZINE-4-THIONE COMPOUNDS

[75] Inventors: Kevin L. Rollick; Joseph A. Kuczkowski, both of Munroe Falls, Ohio

[73] Assignee: The Goodyear Tire & Rubber Company, Akron, Ohio

[21] Appl. No.: 58,474

[22] Filed: Jun. 5, 1987

[51] Int. Cl.$^4$ .............................................. D06P 5/02
[52] U.S. Cl. ........................................ 8/442; 8/566; 8/567; 8/575; 8/924
[58] Field of Search ................... 8/442, 566, 567, 575

[56] References Cited

U.S. PATENT DOCUMENTS

| | | | |
|---|---|---|---|
| 3,822,996 | 7/1974 | Lofquist et al. | 8/585 |
| 4,304,568 | 12/1981 | Johnson et al. | 8/568 |
| 4,362,874 | 12/1982 | Kalk et al. | 8/442 |
| 4,631,066 | 12/1986 | Minemura et al. | 8/115.56 |

OTHER PUBLICATIONS

"The Structure and Properties of Some Urons and Thiourons", C. D. Egginton and C. P. Vale, Textile Research Journal, 1969, vol. 39, (No. 2), pp. 140–147.

*Primary Examiner*—A. Lionel Clingman
*Attorney, Agent, or Firm*—D. O. Nickey

[57] ABSTRACT

This invention relates to the use of compounds such as 3,5-dibutyl-1,3,5-oxadiazine-4-thione and tetrahydro-5-(2-butyl)-(S)-triazinethione as stabilizers to improve the dye fastness of colored fibers.

14 Claims, No Drawings

STABILIZERS FOR IMPROVING THE OZONE FASTNESS OF DYES WITH OXADIAZINE-4-THIONE OR TRIAZINE-4-THIONE COMPOUNDS

TECHNICAL FIELD

This invention relates to processes for improving the fastness of dyes through the use of oxadiazine thiones and triazine thiones. More particularly, the invention relates to a method of treating dyed fibers with substituted oxadiazine thiones and substituted triazine thiones so that the dyed fiber will have minimized or reduced ozone fading without a reduction in light stability.

BACKGROUND ART

The fabric industry, especially the carpet industry, is interested in reducing or preventing the fading of dyed fabrics caused by ozone. By fading is meant loss of fastness of the dye; for example, the dye becomes less bright, changes color, or becomes less appealing. For example, a dark blue dye will change to light blue.

Ozone is an allotropic form of oxygen. The molecule of ozone consists of three atoms of oxygen whereas a molecule of oxygen contains only two atoms of oxygen. Ozone is generally present in the air at concentrations from about 1 to 5 parts per hundred million (pphm).

Ozone is an unstable gas with a pungent odor which decomposes to ordinary oxygen. Ozone possesses a powerful bleaching action and oxidizes substances more rapidly than oxygen and promotes spontaneous ignition of many substances. Its presence in air is known to contribute to the characteristic properties of smog. Embrittlement of rubber compounds is accelerated by the presence of traces of ozone in the air.

Ozone is formed in the upper atmosphere by the action of high energy radiation from the sun splitting oxygen molecules into two oxygen atoms. These atoms then combine with oxygen molecules to form ozones ($O_3$). Under conditions of heavy smog, where sunlight acts on a combination of unburned hydrocarbons from gasoline and oxides of nitrogen, the concentration has been known to exceed 10 parts per hundred million. However, even at low ozone concentrations, if the humidity is high enough, ozone fading is known to occur. In addition, ozone can be produced through the electronic irradiation of air or oxygen such as that experienced in the presence of electric motors and electronic devices.

Ozone is an electrophillic reagent, that is it searches out and attacks electron pairs such as those existing in carbon-carbon double bonds. Dyes have a multiplicity of double bonds and perhaps for this reason are sensitive to ozone. The dyes which are attacked are usually anthraquinone type dispersed dyes; although, it is believed that under severe conditions, almost all dyes will be affected by ozone. The dyes in a synthetic fiber such as nylon are most seriously attacked when the dyes are mobile in the synthetic fiber. Cationic dyes are also susceptible. The most sensitive dispersed dyes are usually blue anthraquinone type dyes.

High humidity enhances the noticeable ozone fading. Apparently, moisture provides the dye sufficient mobility to diffuse to the surface of the yarn where the destruction of the dye occurs.

Ozone fading can be decreased by reduction of the specific surface area of the yarn. Ozone fading can also be decreased by changes in polymer morphology and orientation but these techniques are inherently expensive.

A number of chemicals have been called antiozonants in the literature which protect rubber from ozone. Examples are the para-phenylenediamine derivatives and the dihydroquinoline derivatives. In nylon and other synthetic fibers these chemicals seriously discolor the yarn especially after exposure to light thereby severely limiting the use of such chemicals.

U.S. Pat. No. 3,822,996 discloses and claims a method for improving fastness of dyes in fibers dyed with anthraquinone dyes. The method consists of coating said dyed fiber with a compound selected from the group consisting if thiourea and a saturated alkyl substituted thiourea so that from about 0.2 to about 5% on weight of the fiber of said compound remains on said fiber. This patent claims to reduce the ozone degradation of the dye through the use of these water soluble thioureas.

U.S. Pat. No. 3,844,713 discloses alkyl and aryl phosphites useful in inhibiting ozone fading of dyed polyamides. This patent discloses that when from about 0.7% to about 3% of organic phosphites are coated on nylon fiber or are added to the polymer prior to spinning, improved dye fastness is achieved when compared to an untreated dyed nylon fiber.

U.S. Pat. No. 3,859,045 discloses the use of ethoxylated aliphatic tertiary amines to reduce ozone attack on dyes in polyamide fibers. Specifically, this patent is concerned with the use of about 0.1% to about 8% of tertiary amines such as N,N-bis-(2-hydroxyethyl)-2-aminooctadecane. This patent discloses that from about 0.1 to about 8% on weight of fiber of the compounds disclosed will reduce the fading of dyed polycarbonamide fabrics.

U.S. Pat. No. 4,304,568 discloses a method for minimizing ozone fading in dyed polyamides by treating the dyed polyamide with a substituted piperidine thiourea.

U.S. Pat. No. 4,613,334 describes a process for improving the light fastness of dyeings obtained with acid dyes and/or metal complex dyes on polyamide textile materials, by treating the textile with a copper hydroxamate before, during or after dyeing.

U.S. Pat. No. 4,631,066 discloses that light resistant aromatic polyamide fibers can be improved by heat treating the aromatic polyamide fibers in the presence of urea and thiourea.

None of these patents suggest or disclose the use of compounds such as oxadiazine-4-thiones and triazinethiones to prevent ozone degradation of dyes.

DISCLOSURE OF THE INVENTION

This invention relates to a method and composition useful in improving the fastness of dyes when exposed to ozone. The method consists of exposing the dyed fibers to ozone in the presence of oxadiazine-4-thiones and/or triazinethiones.

There is disclosed a method of dyeing synthetic or natural fibers, the improvement comprising coating the fiber with a compound of the structural formula:

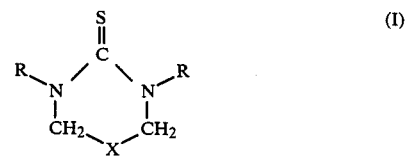

(I)

wherein X is a divalent radical selected from:

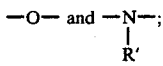

wherein R' and R are independently selected from the group of radicals comprising hydrogen, the radical $-\!(\!CH_2\!-\!CH_2\!)_{\overline{x}}OR''$, alkyl radicals of 1 to 8 carbon atoms, cycloalkyl radicals of 3 to 8 carbon atoms, arylalkyl radicals of 7 to 9 carbon atoms, phenyl radicals and substituted phenyl radicals wherein up to three substituents can be present on the phenyl radical; wherein x is 0, 1, or 2 and wherein R'' is hydrogen, methyl or ethyl radicals;

so that 0.05 to 3% on weight of fiber of said compound is present on said fiber.

There is also disclosed a method of dyeing synthetic fibers, the improvement comprising adding a compound of claim 1 to the polymer which forms said synthetic fiber before spinning, said compound remaining in said fibers in an amount from 0.05 to 3% on the weight of the fiber.

There is further disclosed a process for improving the color fastness of dyeings of synthetic or natural textile materials by treating the textile, before, during or after dyeing with at least one compound of the formula:

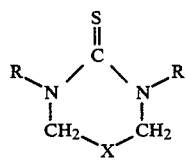 (I)

wherein X is a divalent radical selected from:

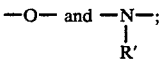

wherein R' and R are independently selected from the group of radicals comprising hydrogen, the radical $-CH_2\!-\!(\!CH_2\!)_{\overline{x}}OR''$, alkyl radicals of 1 to 8 carbon atoms, cycloalkyl radicals of 3 to 8 carbon atoms, arylalkyl radicals of 7 to 9 carbon atoms, phenyl radicals and substituted phenyl radicals wherein up to three substituents can be present on the phenyl radical; wherein x is 0, 1, or 2 and wherein R'' is hydrogen, methyl or ethyl radicals;

so that 0.05 to 3% on weight of fiber of said compound is present on said fiber.

There is also disclosed a method of minimizing ozone fading in a dyed polyamide without reducing the light stability of the dyed polyamide comprising:

treating a dyed polyamide with an ozone fade minimizing effective amount of a compound of the structural formula:

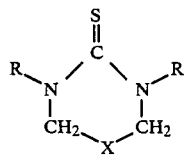 (I)

wherein X is a divalent radical selected from:

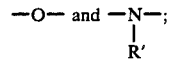

wherein R' and R are independently selected from the group of radicals comprising hydrogen, the radical $-CH_2\!-\!(\!CH_2\!)_{\overline{x}}OR''$, alkyl radicals of 1 to 8 carbon atoms, cycloalkyl radicals of 3 to 8 carbon atoms, arylalkyl radicals of 7 to 9 carbon atoms, phenyl radicals and substituted phenyl radicals wherein up to three substituents can be present on the phenyl radical; wherein x is 0, 1, or 2 and wherein R'' is hydrogen, methyl or ethyl radicals; so that 0.05 to 3% on weight of fiber of said compound is present on said fiber.

Representative of the compounds of structural formula (I) are tetrahydro-3,5-dibutyl-1,3,5-oxadiazine-4-thione;
tetrahydro-5-(2-butyl)-(S)-triazinethione;
tetrahydro-1,3,5-tributyl-(S)-triazinethione;
tetrahydro-5-(2-hydroxyethyl)-(S)-triazinethione;
tetrahydro-5-cyclohexyl-(S)-triazinethione;
tetrahydro-1,3-dimethyl-5-butyl-(S)-triazinethione;
tetrahydro-1,3-diethyl-5-cyclohexyl-(S)-triazinethione;
tetrahydro-3,5-dicyclohexyl-1,3,5-oxadiazine-4-thione;
tetrahydro-3,5-di-(methoxymethyl)-1,3,5-oxadiazine-4-thione; and
tetrahydro-1,3-dibutyl-5-(2-phenylethyl)-(S)-triazinethione.

In one embodiment of the process of this invention at least one compound of structural formula (I) is coated on a synthetic fiber prior to or subsequent to dyeing in amounts from 0.05% to 3% based on the weight of the fiber. Alternatively, the compounds of structural formula (I) can be added to the polymer so that the yarns made therefrom contain 0.05% to 3% by weight of the compounds recited herein. The rate of fading of the dye is substantially reduced by the incorporation into or coating of the fiber with the compounds of this invention. It is possible to treat the fiber before dyeing and use the resulting product as an intermediate material for final dyeing which will possess a built-in resistance to ozone fading. The compounds of this invention can be incorporated in the spin finish, in the oven-finish prior to dyeing or sprayed in solutions or applied as a foam to a dyed fabric.

The present invention is applicable to any type of fiber but the benefits of the invention are most remarkably exhibited when the dyed fabric material is made of a synthetic fiber such as nylon fibers, polyester fibers, acrylic fibers, polypropylene fibers, cellulose acetate fibers, polyvinyl alcohol fibers and the like. The form of the fiber, fabric, or carpet, as the case may be, is not particularly limitative. Woven cloths, including knit fabrics and nonwoven fabrics as well as threads and yarns will benefit from the use of the instant invention. These fabric materials may be made of two or more kinds of fibers including natural fibers. In one embodiment of this invention the fiber or fabric is formed and dyed before being subjected to the method of the present invention. The kind of dye used is not particularly limitative, including any commercially available ones used for dyeing. Although, it should be noted that the effect of this invention for increasing the ozone resistance of a dye is most strongly exhibited when the fiber material is dyed blue in color.

The rate of fading of the dye in fibers, particularly nylons dyed with dispersed or cationic dyes is substantially reduced through the use of the compounds of the above formula and are effective without discoloring the yarn or fiber.

BEST MODE FOR CARRYING OUT THE INVENTION

Without limitation, some of the preferred embodiments of this invention are set forth in the following examples. The method of testing for ozone fading was similar to the AATCC Test Method 129-1975 as set forth on page 146 of the American Association of Textile Chemists and Colorists Technical Manual.

PREPARATION OF COMPOUNDS OF STRUCTURAL FORMULA (I)

EXAMPLE 1

Preparation of Tetrahydro-5-(2-butyl)-(S)-triazinethione

A one liter three neck round bottom flask was charged with thiourea (152.2 g; 2.0 mol) and aqueous formalin (328 g; 4.0 mol). The flask was fitted with a mechanical stirrer, condenser and an addition funnel containing sec-butyl amine (146.3 g; 2.0 mol). The flask was heated to about 60° C. and addition of the amine begun. The rate of addition was controlled to maintain a gentle reflux. When addition was complete the mixture was refluxed an additional three hours then poured into a beaker and allowed to crystallize. The solid mass was broken up, filtered, reslurried in 1500 ml of water, refiltered and dried. Yield 290 g (84% based on thiourea charged) with mp-145°-7° C. and characterized by NMR to be tetrahydro-5-(2-butyl)-(S)-triazinethione.

EXAMPLE 2

Tetrahydro-1,3,5-tributyl-(S)-triazinethione

A two liter three neck round bottom flask was charged with N,N'-dibutylthiourea (470 g; 2.5 mol), aqueous formalin (410 g; 5.0 mol) and 300 ml toluene. The flask was fitted with a mechanical stirrer, additional funnel, Claisen adaptor, thermometer, Dean-Stark trap and condenser. Butyl amine (183 g; 2.5 mol) was added over one hour via the addition funnel and the mixture was then heated just to reflux for an additional hour. Thereafter heating was increased to drive the water of solution and water of reaction overhead as the toluene azeotrope. When the theoretical amount of water had been collected, the Dean-Stark trap and condenser were replaced with a distillation head and the toluene distilled out under vacuum (30 mm Hg) to a pot temp. of 100° C. The product, a light yellow oil was then suction filtered and bottled. Yield 683 g of a liquid, characterized by NMR (96%).

EXAMPLE 3

Preparation of Tetrahydro-3,5-dibutyl-1,3,5-oxadiazine-4-thione 18 grams of formalin (37% by weight aqueous solution of formaldehyde), 18.8 grams of N,N'-dibutylthiourea, 0.5 grams of toluene sulfonic acid and 50 mls of toluene were charged to 250 ml 3-neck reaction flask fitted with a Dean-Stark trap, a stirrer and a thermometer. The mixture was heated to reflux and the water/toluene azeotrope was taken overhead and the toluene returned to the reaction flask through the Dean-Stark trap. The mixture was heated at reflux until the theoretical amount of water of solution and of reaction had been collected.

The toluene was stripped out under vacuum (30 mm Hg. and pot temperature of 100° C.). The product was filtered to remove insoluble by-products and stored for later use. The reaction yielded 22 grams of a liquid product for a 96% yield based on thiourea charged and characterized by NMR.

EXAMPLE 4

Testing of Compounds of Structural Formula (I)

The compounds prepared in Examples 1–3 and others were formulated into emulsions prior to their topical application to a previously dyed carpet sample. The emulsions were prepared using an Eppenbach mixer which is a high shear homogenizer. 25 grams of the subject compound was combined with 25 grams of toluene and 2.5 grams of the surfactant Calsoft LAS-99 (a linear alkyl sulfonate marketed by the Calgon Corporation). Agitation was begun and then 46.5 grams of water containing 1 gram of KOH was added to the toluene/surfactant solution. After vigorous agitation for a few minutes, the emulsion was complete and the sample was ready for application.

The prepared emulsions were then applied to a swatch of carpet that was composed of Nylon 66 yarn which had been dyed with acid blue number 277. The carpet samples were then sprayed with the prepared emulsions and dried. Two or more applications of the emulsions were made to obtain 0.2% weight gain on the weight of the substrate or carpet sample after drying. The test specimens and control samples were then simultaneously exposed to ozone in an atmosphere which was maintained at 85±5% relative humidity and at a temperature of 40±5° C. until the control sample evidenced a color change corresponding to that of a standard of fading. The cycles were repeated 2 times.

This test is designed to determine the resistance of the color to the action of ozone in an atmosphere of elevated temperatures and high humidity. The fading of certain dyes does not readily take place at humidities below 80%. A test at high humidities is required to produce color change that predicts service fading under warm, humid conditions.

In addition to the untreated control sample that was exposed to the ozone, an untreated, unexposed control was also prepared.

The treated sample and the control to be exposed were suspended in the exposure chamber maintained at 85±5% relative humidity and a temperature of 40±5° C. Ozone was present in a concentration ranging from 10 to 35 parts per hundred million which usually produced one cycle of fading in 3 to 28 hours of testing.

At the end of 2 cycles, the samples were removed from the test chamber and immediately compared with the untreated, unexposed control.

The data presented in the following table is a measure of the color change. $\Delta E$ is a measure of color change, a smaller $\Delta E$ representing less fading. More specifically, the color difference $\Delta E$ equals square root of $(\Delta L)^2 + (\Delta a)^2 + (\Delta b)^2$. Readings were taken on a Gardner Colorimeter XL-20. One skilled in the art will appreciate how the numbers are generated and what they mean.

TABLE I

Ozone testing of compounds at 0.2% by weight based on weight of carpet.

| Compound | Original | | | Aged | | | ΔE |
|---|---|---|---|---|---|---|---|
| | L | a | b | L | a | b | |
| Control+ | 45.72 | 1.76 | 2.39 | 47.75 | 2.86 | 4.66 | 3.24 |
| TBTT | 43.82 | 1.66 | 2.36 | 43.47 | 1.91 | 2.88 | 0.67 |
| DBOXT | 43.70 | 1.66 | 2.45 | 44.16 | 1.49 | 2.98 | 0.72 |
| Quinozo 133* | 42.19 | 1.55 | 2.34 | 44.50 | 1.75 | 2.90 | 2.39 |
| Control #2 | 44.16 | 1.75 | 2.63 | 48.99 | 4.77 | 7.66 | 7.60 |
| HETT | 43.59 | 1.48 | 2.27 | 43.47 | 2.44 | 3.05 | 1.24 |
| DMOXT | 43.36 | 1.74 | 2.27 | 44.72 | 3.07 | 4.22 | 2.72 |
| SBTT | 46.58 | 1.95 | 3.20 | 44.05 | 2.10 | 2.98 | 2.54 |

*Quinozo 133 is a material made by Wi-Chem Inc. marketed as an ozone fade resist for carpeting.
+Control - no treatment.
TBTT = Tetrahydro-1,3,5-tributyl-(S)—triazinethione
DBOXT = Tetrahydro-3,5-dibutyl-1,3,5-oxadiazine-4-thione
HETT = Tetrahydro-5-(2-hydroxyethyl)-(S)—triazinethione
DMOXT = Tetrahydro-3,5-dimethyl-1,3,5-oxadiazine-4-thione
SBTT = Tetrahydro-5-(2-butyl)-(S)—triazinethione The data indicate that the compounds of this invention are effective in lessening the ozone degradation of the dye.

As mentioned previously, numerous known materials are effective antiozonants, however, many of these compounds are detrimental to the finished product when exposed to UV light since they produce color bodies or fail to prevent (even enhance) the fading of the dye.

In a manner similar to that for the ozone testing, controls and compounds of this invention were tested for color fastness after exposure to UV light. It was surprising that the compounds of this invention not only lessen ozone degradation but also produced no color bodies and lessened dye fading upon exposure to UV light.

To those skilled in the art it should be appreciated that the compounds of this invention may be incorporated into the fiber, applied in conjunction with the dyeing process or applied subsequent to dyeing by dipping and squeezing, by spraying with nozzles or through the use of a head that applies the compound as the carpet moves or as a foam.

The following are examples of the subject additives and their behavior on being added to nylon polymer chips, spun into yarn, dyed and exposed to ozone.

The polymer is a polycaprolactam of about 20,000 number average molecular weight, marketed by the Du Pont Chemical Company as Nylon 6 which contains about 10 ppm of maganese as maganese chloride, about 25 ppm of phosphorus as hypophosphorous acid, and about 0.13% $TiO_2$ as a delusterant. The additives are added to the nylon polymer immediately before spinning.

The polymer is spun into 16 filaments having a total denier of about 230 at a spinning temperature of about 260° to 265° C. The yarn is drawn at a ratio of 3.2.

The yarn is knitted into sleeves and dyed with acid blue number 277.

The sleeves are then subjected to an ozone atmosphere of about 35 pphm (parts per hundred million) ozone at a temperature of 40° C. at a relative humidity of at least 80% for two cycles. A cycle is that amount of exposure which occurs when a control shows a specified color change as measured by a Colorimeter. It is submitted that upon exposure to ozone, the compounds of this invention will lessen the degradation of the dye.

INDUSTRIAL APPLICABILITY

The compounds and method of the present invention have demonstrated utility as stabilizers for dyes. The compositions and method of the instant invention lessen the degradative effects of ozone. The present invention would have obvious utility to those skilled in the field of dyeing fabrics. A particularly beneficial property is the nonstaining characteristic of these compounds wherein the compounds do not, after exposure to ozone, impart a deleterious color to the dyed material.

Those skilled in the art of dyeing fabrics will readily appreciate the beneficial properties that the compounds of the instant invention can impart to fabrics dyed with materials that are subject to ozone degradation.

While certain representative embodiments and details have been shown for the purpose of illustrating the invention, it will be apparent to those skilled in this art that various changes and modifications may be made herein without departing from the scope of the invention.

What is claimed is:

1. A method of dyeing synthetic or natural fibers, the improvement comprising coating the fiber with a compound of the structural formula:

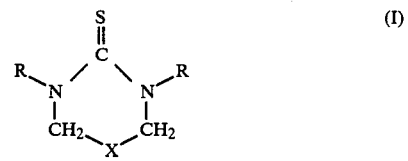

wherein X is a divalent radical selected from:

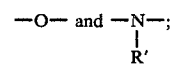

wherein R' and R are independently selected from the group of radicals comprising hydrogen, the radical —$CH_2$—$(CH_2)_x$OR'', alkyl radicals of 1 to 8 carbon atoms, cycloalkyl radicals of 3 to 8 carbon atoms, arylalkyl radicals of 7 to 9 carbon atoms, phenyl radicals and substituted phenyl radicals wherein up to 3 substituents can be present on the phenyl radical; wherein x is 0, 1, or 2 and wherein R'' is hydrogen, methyl or ethyl radicals;

so that 0.05 to 3% on weight of fiber of said compound is present on said fiber.

2. The method of claim 1 wherein R is a butyl radical and X is the radical —O—.

3. The method of claim 1 wherein R is a butyl radical and X is the rdical >N—$C_4H_9$.

4. The method of claim 1 wherein R is hydrogen and X is the radical:

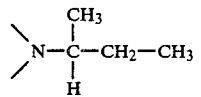

5. A method of dyeing synthetic fibers, the improvement comprising adding an oxadiazine-4-thione to the polymer which forms said synthetic fiber before spinning, said oxadiazine-4-thione remaining in said fibers in an amount from 0.05 to 3% on the weight of the fiber.

6. A process for improving the color fastness of dyeings on synthetic or natural textile materials by treating the textile, before, during or after dyeing with at least one compound of the formula:

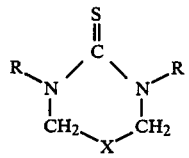

wherein X is a divalent radical selected from:

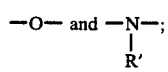

wherein R' and R are independently selected from the group of radicals comprising hydrogen, the radical —CH$_2$—(CH$_2$)$_x$OR", alkyl radicals of 1 to 8 carbon atoms, cycloalkyl radicals of 3 to 8 carbon atoms, arylalkyl radicals of 7 to 9 carbon atoms, phenyl radicals and substituted phenyl radicals wherein up to 3 substituents can be present on the phenyl radical; wherein x is 0, 1, or 2 and wherein R" is hydrogen, methyl or ethyl radicals;
so that 0.05 to 3% on weight of fiber of said compound remains on said fiber after dyeing.

7. The process of claim 6, wherein R is a butyl radical and X is the radical —O—.

8. The process of claim 6 wherein R is a butyl radical and X is the radical >N—C$_4$H$_9$.

9. The process of claim 6 wherein R is hydrogen and X is the radical:

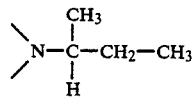

10. A method of minimizing ozone fading in a dyed polyamide without reducing the light stability of the dyed polyamide comprising:
treating a dyed polyamide with an ozone fade minimizing effective amount of a compound of the structural formula:

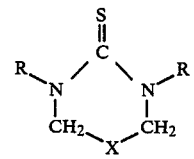

wherein X is a divalent radical selected from:

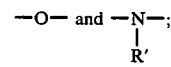

wherein R' and R are independently selected from the group of radicals comprising hydrogen, the radical —CH$_2$—(CH$_2$)$_x$OR", alkyl radicals of 1 to 8 carbon atoms, cycloalkyl radicals of 3 to 8 carbon atoms, arylalkyl radicals of 7 to 9 carbon atoms, phenyl radicals and substituted phenyl radicals wherein up to 3 substituents can be present on the phenyl radical; wherein x is 0, 1, or 2 and wherein R" is hydrogen, methyl or ethyl radicals;
so that 0.05 to 3% on weight of fiber of said compound is present on said fiber.

11. The method of claim 1 wherein the fiber is a dyed polyamide fiber.

12. The method of claim 6 wherein R is a butyl radical and X is the radical >N—C$_4$—H$_9$.

13. The method of claim 6 wherein R is hydrogen and X is the radical:

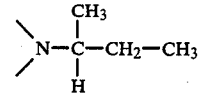

14. Dyed polyamide treated in accordance with the method of claim 6.

* * * * *

UNITED STATES PATENT AND TRADEMARK OFFICE
CERTIFICATE OF CORRECTION

PATENT NO. : 4,737,155

DATED : April 12, 1988

INVENTOR(S) : Rollick et al

It is certified that error appears in the above-identified patent and that said Letters Patent is hereby corrected as shown below:

At Col. 1, line 39 delete "ozones" and insert therefor --ozone--.

At Col. 2, line 14 delete "if" and insert therefor --of--.

At Col. 3, line 9, delete "$-(CH_2-CH_2)_x-OR$" and insert therefor --$-CH_2-(CH_2)_x-OR$"--.

At Col. 8, line 55, delete "rdical" and replace therefor --radical--.

Signed and Sealed this

Thirty-first Day of January, 1989

Attest:

DONALD J. QUIGG

*Attesting Officer*  *Commissioner of Patents and Trademarks*